(12) United States Patent
Yatesenko et al.

(10) Patent No.: US 7,497,621 B2
(45) Date of Patent: Mar. 3, 2009

(54) SYSTEM AND METHOD FOR INTEGRATION OF A CALIBRATION TARGET INTO A C-ARM

(75) Inventors: Dimitri Victorovich Yatesenko, Salt Lake City, UT (US); Jon Thomas Lea, Hampstead, NH (US); Charles Frederick Lloyd, Reading, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/971,628

(22) Filed: Jan. 9, 2008

(65) Prior Publication Data

US 2008/0107241 A1 May 8, 2008

Related U.S. Application Data

(62) Division of application No. 11/271,604, filed on Nov. 10, 2005, now Pat. No. 7,344,307.

(60) Provisional application No. 60/627,251, filed on Nov. 12, 2004.

(51) Int. Cl.
*G01D 18/00* (2006.01)
(52) U.S. Cl. ........................ 378/207; 378/205
(58) Field of Classification Search ......... 378/205–207, 378/62
See application file for complete search history.

(56) References Cited

U.S. PATENT DOCUMENTS

2004/0245447 A1* 12/2004 Karasawa ................ 250/252.1

* cited by examiner

*Primary Examiner*—Hoon Song
(74) *Attorney, Agent, or Firm*—McAndrews, Held & Malloy, Ltd.; Peter J. Vogel; Michael A. Dellapenna

(57) ABSTRACT

Certain embodiments of the present invention provide a method and system for improved calibration of an image acquisition device. Certain embodiments of the system include an image acquisition device for obtaining at least one image of an object and a calibration fixture positioned in relation to the image acquisition device. The calibration fixture includes a radiotranslucent material providing low frequency content for characterizing the image acquisition device. In an embodiment, the calibration fixture includes a plurality of peaks and valleys to create a low frequency signal for characterizing the image acquisition device. The calibration fixture may be positioned between the image acquisition device and an energy source such that a distance between the image acquisition device and the calibration fixture is minimized. In certain embodiments, a grating or other calibration fixture may be used to generate a moiré pattern to calibrate the image acquisition device.

23 Claims, 11 Drawing Sheets

FIG. 5
530 
510 
520 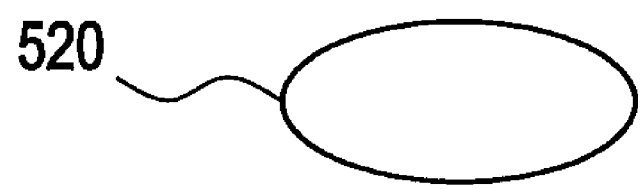

SYSTEM AND METHOD FOR INTEGRATION OF A CALIBRATION TARGET INTO A C-ARM

RELATED APPLICATIONS

The present application relates to and claims the benefit of priority as a divisional of U.S. patent application Ser. No. 11/271,604, filed on Nov. 10, 2005, entitled "System and Method for Integration of a Calibration Target into a C-Arm," which claims priority to U.S. Provisional Application No. 60/627,251, filed on Nov. 12, 2004, each of which is herein incorporated by reference in its entirety.

BACKGROUND OF THE INVENTION

The present invention generally relates to imaging and image-guided navigation. In particular, the present invention relates to a system and method for improved calibration of equipment used in imaging and image-guided operations.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may also be used to track the position of items other than medical instruments in a variety of applications. That is, a tracking system may be used in other settings where the position of an instrument in an object or an environment is difficult to accurately determine by visual inspection. For example, tracking technology may be used in forensic or security applications. Retail stores may use tracking technology to prevent theft of merchandise. In such cases, a passive transponder may be located on the merchandise. A transmitter may be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking systems are also often used in virtual reality systems or simulators. Tracking systems may be used to monitor the position of a person in a simulated environment. A transponder or transponders may be located on a person or object. A transmitter emits an excitation signal and a transponder produces a response signal. The response signal is detected by a receiver. The signal emitted by the transponder may then be used to monitor the position of a person or object in a simulated environment.

Tracking systems may be ultrasound, inertial position, or electromagnetic tracking systems, for example. Electromagnetic tracking systems may employ coils as receivers and transmitters. Typically, an electromagnetic tracking system is configured in an industry-standard coil architecture (ISCA). ISCA uses three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

The ISCA tracker architecture uses a three-axis dipole coil transmitter and a three-axis dipole coil receiver. Each three-axis transmitter or receiver is built so that the three coils exhibit the same effective area, are oriented orthogonally to one another, and are centered at the same point. If the coils are small enough compared to a distance between the transmitter and receiver, then the coil may exhibit dipole behavior. Magnetic fields generated by the trio of transmitter coils may be detected by the trio of receiver coils. Using three approximately concentrically positioned transmitter coils and three approximately concentrically positioned receiver coils, for example, nine parameter measurements may be obtained. From the nine parameter measurements and one known position or orientation parameter, a position and orientation calculation may determine position and orientation information for each of the transmitter coils with respect to the receiver coil trio with three degrees of freedom.

In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

Several areas of surgery involve very precise planning and control for placement of an elongated probe or other article in tissue or bone that is internal or difficult to view directly. In particular, for brain surgery, stereotactic frames that define an entry point, probe angle and probe depth are used to access a site in the brain, generally in conjunction with previously compiled three-dimensional diagnostic images, such as MRI, PET or CT scan images, which provide accurate tissue images. For placement of pedicle screws in the spine, where visual and fluoroscopic imaging directions may not capture an axial view to center a profile of an insertion path in bone, such systems have also been useful.

When used with existing CT, PET or MRI image sets, previously recorded diagnostic image sets define a three dimensional rectilinear coordinate system, either by virtue of their precision scan formation or by the spatial mathematics of their reconstruction algorithms. However, it may be desirable to correlate the available fluoroscopic views and anatomical features visible from the surface or in fluoroscopic images with features in the 3-D diagnostic images and with external coordinates of tools being employed. Correlation is often done by providing implanted fiducials and adding externally visible or trackable markers that may be imaged. Using a keyboard or mouse, fiducials may be identified in the various images. Thus, common sets of coordinate registration points may be identified in the different images. The common sets of coordinate registration points may also be trackable in an automated way by an external coordinate measurement device, such as a suitably programmed off-the-shelf optical tracking assembly. Instead of imageable fiducials, which may for example be imaged in both fluoroscopic and MRI or CT images, such systems may also operate to a large extent with simple optical tracking of the surgical tool and may employ an initialization protocol wherein a surgeon touches or points at a number of bony prominences or other recognizable anatomic features in order to define external coordinates in relation to a patient anatomy and to initiate software tracking of the anatomic features.

Generally, image-guided surgery systems operate with an image display which is positioned in a surgeon's field of view and which displays a few panels such as a selected MRI image and several x-ray or fluoroscopic views taken from different angles. Three-dimensional diagnostic images typically have a spatial resolution that is both rectilinear and accurate to within a very small tolerance, such as to within one millimeter or less. By contrast, fluoroscopic views may be distorted. The fluoroscopic views are shadowgraphic in that they represent the density of all tissue through which the conical x-ray beam has passed. In tool navigation systems, the display visible to the surgeon may show an image of a surgical tool, biopsy instrument, pedicle screw, probe or other device projected onto a fluoroscopic image, so that the surgeon may visualize the orientation of the surgical instrument in relation to the imaged patient anatomy. An appropriate reconstructed CT or MRI image, which may correspond to the tracked coordinates of the probe tip, may also be displayed.

Among the systems which have been proposed for effecting such displays, many rely on closely tracking the position and orientation of the surgical instrument in external coordinates. The various sets of coordinates may be defined by robotic mechanical links and encoders, or more usually, are defined by a fixed patient support, two or more receivers such as video cameras which may be fixed to the support, and a plurality of signaling elements attached to a guide or frame on the surgical instrument that enable the position and orientation of the tool with respect to the patient support and camera frame to be automatically determined by triangulation, so that various transformations between respective coordinates may be computed. Three-dimensional tracking systems employing two video cameras and a plurality of emitters or other position signaling elements have long been commercially available and are readily adapted to such operating room systems. Similar systems may also determine external position coordinates using commercially available acoustic ranging systems in which three or more acoustic emitters are actuated and their sounds detected at plural receivers to determine their relative distances from the detecting assemblies, and thus define by simple triangulation the position and orientation of the frames or supports on which the emitters are mounted. When tracked fiducials appear in the diagnostic images, it is possible to define a transformation between operating room coordinates and the coordinates of the image.

In general, the feasibility or utility of a system of this type depends on a number of factors such as cost, accuracy, dependability, ease of use, speed of operation and the like. Intraoperative x-ray images taken by C-arm fluoroscopes alone have both a high degree of distortion and a low degree of repeatability, due largely to deformations of the basic source and camera assembly, and to intrinsic variability of positioning and image distortion properties of the camera. In an intraoperative sterile field, such devices are typically draped, which may impair optical or acoustic signal paths of the signal elements they employ to track the patient, tool or camera.

More recently, a number of systems have been proposed in which the accuracy of the 3-D diagnostic data image sets is exploited to enhance accuracy of operating room images, by matching these 3-D images to patterns appearing in intraoperative fluoroscope images. These systems may use tracking and matching edge profiles of bones, morphologically deforming one image onto another to determine a coordinate transform, or other correlation process. The procedure of correlating the lesser quality and non-planar fluoroscopic images with planes in the 3-D image data sets may be time-consuming. In techniques that use fiducials or added markers, a surgeon may follow a lengthy initialization protocol or a slow and computationally intensive procedure to identify and correlate markers between various sets of images. All of these factors have affected the speed and utility of intraoperative image guidance or navigation systems.

Correlation of patient anatomy or intraoperative fluoroscopic images with precompiled 3-D diagnostic image data sets may also be complicated by intervening movement of the imaged structures, particularly soft tissue structures, between the times of original imaging and the intraoperative procedure. Thus, transformations between three or more coordinate systems for two sets of images and the physical coordinates in the operating room may involve a large number of registration points to provide an effective correlation. For spinal tracking to position pedicle screws, the tracking assembly may be initialized on ten or more points on a single vertebra to achieve suitable accuracy. In cases where a growing tumor or evolving condition actually changes the tissue dimension or position between imaging sessions, further confounding factors may appear.

When the purpose of image guided tracking is to define an operation on a rigid or bony structure near the surface, as is the case in placing pedicle screws in the spine, the registration may alternatively be effected without ongoing reference to tracking images, by using a computer modeling procedure in which a tool tip is touched to and initialized on each of several bony prominences to establish their coordinates and disposition, after which movement of the spine as a whole is modeled by optically initially registering and then tracking the tool in relation to the position of those prominences, while mechanically modeling a virtual representation of the spine with a tracking element or frame attached to the spine. Such a procedure dispenses with the time-consuming and computationally intensive correlation of different image sets from different sources, and, by substituting optical tracking of points, may eliminate or reduce the number of x-ray exposures used to effectively determine the tool position in relation to the patient anatomy with the reasonable degree of precision.

However, each of the foregoing approaches, correlating high quality image data sets with more distorted shadowgraphic projection images and using tracking data to show tool position, or fixing a finite set of points on a dynamic anatomical model on which extrinsically detected tool coordinates are superimposed, results in a process whereby machine calculations produce either a synthetic image or select an existing data base diagnostic plane to guide the surgeon in relation to current tool position. While various jigs and proprietary subassemblies have been devised to make each individual coordinate sensing or image handling system easier to use or reasonably reliable, the field remains unnecessarily complex. Not only do systems often use correlation of diverse sets of images and extensive point-by-point initialization of the operating, tracking and image space coordinates or features, but systems are subject to constraints due to the proprietary restrictions of diverse hardware manufacturers, the physical limitations imposed by tracking systems and the complex programming task of interfacing with many different image sources in addition to determining their scale, orientation, and relationship to other images and coordinates of the system.

Several proposals have been made that fluoroscope images be corrected to enhance their accuracy. This is a complex undertaking, since the nature of the fluoroscope's 3D to 2D projective imaging results in loss of a great deal of information in each shot, so the reverse transformation is highly underdetermined. Changes in imaging parameters due to camera and source position and orientation that occur with each shot further complicate the problem. This area has been addressed to some extent by one manufacturer which has provided a more rigid and isocentric C-arm structure. The added positional precision of that imaging system offers the prospect that, by taking a large set of fluoroscopic shots of an immobilized patient composed under determined conditions, one may be able to undertake some form of planar image reconstruction. However, this appears to be computationally very expensive, and the current state of the art suggests that while it may be possible to produce corrected fluoroscopic image data sets with somewhat less costly equipment than that used for conventional CT imaging, intra-operative fluoroscopic image guidance will continue to involve access to MRI, PET or CT data sets, and to rely on extensive surgical input and set-up for tracking systems that allow position or image correlations to be performed.

Thus, it remains highly desirable to utilize simple, low-dose and low cost fluoroscope images for surgical guidance, yet also to achieve enhanced accuracy for critical tool positioning.

Magnetic fields may affect x-rays and other image energy sources. Additionally, gravity may affect geometry of an x-ray system. Focal length and piercing point of x-rays may change depending upon the position of a C-arm or other mobile component of an imaging system. A difference between an imaging angle and an angle of the Earth's magnetic field may cause distortion that affects a resulting image. Additionally, an operator or patient may bump the C-arm or other component of an imaging system during operation or positioning, which may affect a resulting image. Thus, there is a need for improved calibration to reduce an effect of distortion on an image.

Registration is a process of correlating two coordinate systems, such as a patient image coordinate system and an electromagnetic tracking coordinate system. Several methods may be employed to register coordinates in imaging applications. "Known" or predefined objects are located in an image. A known object includes a sensor used by a tracking system. Once the sensor is located in the image, the sensor enables registration of the two coordinate systems.

U.S. Pat. No. 5,829,444 by Ferre et al., issued on Nov. 3, 1998, refers to a method of tracking and registration using a headset, for example. A patient wears a headset including radiopaque markers when scan images are recorded. Based on a predefined reference unit structure, the reference unit may then automatically locate portions of the reference unit on the scanned images, thereby identifying an orientation of the reference unit with respect to the scanned images. A field generator may be associated with the reference unit to generate a position characteristic field in an area. When a relative position of a field generator with respect to the reference unit is determined, the registration unit may then generate an appropriate mapping function. Tracked surfaces may then be located with respect to the stored images.

However, registration using a reference unit located on the patient and away from the fluoroscope camera introduces inaccuracies into coordinate registration due to distance between the reference unit and the fluoroscope. Additionally, the reference unit located on the patient is typically small or else the unit may interfere with image scanning. A smaller reference unit may produce less accurate positional measurements, and thus impact registration.

Typically, a reference frame used by a navigation system is registered to an anatomy prior to surgical navigation. Registration of the reference frame impacts accuracy of a navigated tool in relation to a displayed fluoroscopic image. Therefore, a system and method that improve registration of the reference frame would be highly desirable. Improved registration may help to decrease error between reference frames and improve navigated tracking accuracy.

Aspects of imaging system variability may be addressed using tracking elements in conjunction with a calibration fixture or correction assembly to provide fluoroscopic images of enhanced accuracy for tool navigation and workstation display. The calibration fixture and use of the calibration fixture in tracking are described in further detail in U.S. Pat. No. 6,484,049 by Seeley et al., issued on Nov. 19, 2002, and U.S. Pat. No. 6,490,475 by Seeley et al., issued on Dec. 3, 2002. A reference unit may also be used, as described in further detail in U.S. Pat. No. 5,829,444 by Ferre et al., issued on Nov. 3, 1998. Radiopaque calibration markers, such as ball bearings (BBs), are used to calibrate components in an imaging system.

Calibration fixtures or reference units may be used to reduce registration error for a registration or reference frame and improve accuracy in navigated tracking of an instrument. A reference frame may include a calibration fixture. The calibration fixture may be removably attached in a precise position with respect to the camera or to the patient. One or more tracking elements or markers may be included in the calibration fixture. A tracking element may be a point-origin defining tracking element that identifies spatial coordinates and/or orientation of the tracking element and, therefore, an object to which the tracking element is attached. Thus, a tracking element may with one or more measurements determine a position of markers in the calibration fixture and a position and orientation of the fixture itself or a surface to which the fixture is attached.

Current fixtures use very radiopaque, discrete markers in radiolucent material. Thus, a need exists for improved calibration fixtures and calibration markers. Typically, an array of discrete, dark markers, such as ball bearings, are arranged in multiple planes for use in calibration. A calibration system watches for spikes and attenuations in a recorded curve to identify the ball bearings in the image.

Examples of calibration fixtures are described in U.S. Pat. No. 5,829,444, mentioned above, and a U.S. Patent Application entitled "Method and System for Improved Correction of Registration Error in a Fluoroscopic Image", by Douglas Johnson and Lewis Levine, filed on Jun. 2, 2004 (Ser. No. 10/859,767), which is herein incorporated by reference. FIG. 1 illustrates an example of a calibration fixture 50 that may be used in improved coordinate frame registration and tracking accuracy. The fixture 50 may include one or more marker plates or sheets 52 of radiolucent material, such as an acrylic (e.g., Lexan) or polymer plate. Each sheet holds an array of radiopaque point-like markers 54, such as stainless steel balls (e.g., ball bearings or BBs). The one or more plates holding the BBs may be affixed at or near to the face of the camera imaging assembly so as to allow accurate calibration of the entire volume of interest while occupying a sufficiently small space that the camera may be positioned closely to the patient. The illustrated calibration fixture 50 includes a releasable clamp assembly 51, with a clamp handle 51a, or other attachment device configured to attach directly on or over the face of the camera assembly. Additionally, the calibration fixture 50 may include an attachment point for a tracking sensor. The structure of the calibration fixture 50 is predefined and modeled to serve as a reference. That is, radiopaque markers, sensors, and/or other structures in the calibration fixture 50 are located and measured during manufacturing or prior to use in imaging. Characterization data from the structure of the calibration fixture 50 is used to register the image and navigation coordinate systems. For example, characterization data describing reference markers in the fixture 50 is loaded into a tracking system prior to scanning. Tight manufacturing tolerances and/or modeling are used to model the calibration fixture 50 as a reliable reference to measure and correct registration error.

FIG. 2 illustrates another example of a calibration fixture 60 that may be used in improved coordinate frame registration and tracking accuracy. The calibration fixture 60 may be affixed at or near an object being imaged, such as a patient. The calibration fixture 60 includes an attachment point 61 for a tracking sensor. The calibration fixture 60 includes an array of radiopaque calibration markers, such as BBs. In an embodiment, a size of the second calibration fixture 60 is minimized to reduce an impact of the fixture 60 on a resulting image. Holes or openings, for example, may also be left in the calibration fixture 60, as shown in FIG. 4, to reduce its profile and impact on imaging. The structure of the second calibration fixture 60 is predefined and modeled to serve as a reference. That is, radiopaque markers, sensors, and/or other structures in the calibration fixture 60 are located and measured during manufacturing or prior to use in imaging. Characterization data from the structure of the calibration fixture 60 is used to register the image and navigation coordinate systems. For example, characterization data describing reference markers in the fixture 60 is loaded into a tracking system prior to scanning. Tight manufacturing tolerances and/or modeling are used to model the calibration fixture 50 as a reliable reference to measure and correct registration error.

The BBs or other radiopaque or calibration markers may be of different sizes in the different planes or may be of the same size. In an embodiment, the BBs are of the same size, e.g., about one or two millimeters in diameter. The BBs or other markers appear in an image and are discernable from anatomy or other interesting objects.

In an embodiment, a radiopaque object, such as a metal or other material object, for example a BB, may be placed into holes on a radiolucent marker sheet such that all marker coordinates are known. Alternatively, marker plates may be manufactured by circuit board microlithography techniques to provide desired patterns of radiopaque markers, for example as metallization patterns, on one or more thin radiolucent films or sheets. The calibration fixtures 50, 60 may also be fabricated as a single block of a suitable radiolucent material with holes drilled to accommodate BBs or other markers. BBs or other markers may be arranged at multiple levels and multiple positions in the fixture.

One suitable radiolucent material is a structural foam of the type used in aircraft wings for lightweight structural rigidity. The radiolucent material may also be employed in separate thin marker-holding sheets. In an embodiment, the selected polymer or foam, and the number and size of the markers, are configured to remain directly in the imaging beam of the fluoroscope device and be imaged in each shot, while the position of the fixture is tracked. The fixture materials are selected to avoid introducing any significant level of x-ray absorption or x-ray scattering by the plates, sheets or block, and the size and number of markers are similarly chosen to avoid excessive shadowing of the overall image, while maintaining a sufficiently dense image level for their detectability, so that both the imaging source radiation level and the resulting image density scale remain comparable to currently desired operating levels. In an embodiment, BBs or other markers are arranged in a pattern at one or more levels, with a different pattern at each level. Further, when more than one array at different depths is used, the patterns may be positioned so that as the source/camera alignment changes, BBs of one pattern cast shadows substantially distinct from those of the other pattern(s). Thus, calibration fixtures 50, 60 are predefined structures known with respect to a tracker.

However, use of BBs or other calibration markers in a fixture may impose distortion or artifacts in resulting images. Although some work has been done to remove such artifacts, some distortion still remains, and there is a need for an improved system and method for reducing artifacts introduced in an image by calibration markers. A system and method for improved calibration and distortion reduction would be highly desirable.

Generally, a goal of intrinsic geometry calibration is to determine a location of an x-ray focal spot in relation to an x-ray detector. On existing x-ray systems, such as fixed-room or mobile C-arms, the focal spot location may vary by 10 mm or more over the full range of motion of the C-arm structure. A source of this variation may be elastic deflection of the C-arm itself, bearing backlash, and other component motions. Knowing the precise location of the focal spot is important for 3D reconstruction and 2D navigation.

As mentioned above, prior geometry calibration procedures use a calibration phantom, which typically is comprised of a number of discrete fiducials arranged in a three-dimensional pattern. One such phantom uses a series of BBs arranged in a helix around an x-ray transparent cylinder. In an offline calibration procedure, images of the phantom are acquired throughout the motion trajectory of the C-arm and the intrinsic geometry parameters are computed. These parameters are assumed to remain unchanged and are used for subsequent in vivo scans. Another method uses one or more planes of BBs or crosshairs affixed to the detector surface. This calibration phantom is used clinically. After an image of the anatomy is taken, the intrinsic parameters are calculated and the image artifacts from the fiducials are removed via image processing techniques.

Both of the methods described suffer from disadvantages. The helical phantom and offline procedure assumes that the parameters will remain unchanged. Wear and damage to the device may affect the accuracy of the stored parameters. Furthermore, there may be situations where the user unknowingly is flexing the C-arm by unintended collision with the operating table. The second method suffers from image degradation from the removal of the image artifacts. Also, the depth of the calibration phantom (e.g., 8-10 cm) compromises the usable patient volume between the x-ray source and detector.

Thus, a system and method that provide intrinsic parameter calculation for a variety of images would be highly desirable. A system and method that minimize image degradation would also be highly desirable. Additionally, a system and method that reduce a source-detector volume would be highly desirable.

BRIEF SUMMARY OF THE INVENTION

Certain embodiments of the present invention provide a method and system for improved calibration of a camera or image acquisition device. Certain embodiments of the system include an image acquisition device for obtaining at least one image of an object and a calibration fixture positioned in relation to the image acquisition device. The calibration fixture includes a radiotranslucent material providing low frequency content for characterizing the image acquisition device.

In an embodiment, the calibration fixture includes a plurality of peaks and valleys to create a low frequency signal for characterizing the image acquisition device. The calibration fixture may be positioned between the image acquisition device and an energy source such that a distance between the image acquisition device and the calibration fixture is minimized. For example, size of an imaging system may be reduced while helping to maximize available patient space.

In an embodiment, the image acquisition device includes a camera positioned on a C-arm. The system may also include at least one tracking device for obtaining at least one of position and orientation data for the calibration fixture. Additionally, the system may include a tool manipulated by an operator using images obtained by the image acquisition device. In an embodiment, the system includes an image processing system for processing at least one image for display.

Certain embodiments of a method for improved calibration of an image acquisition system include acquiring data from a radiotranslucent calibration fixture located near an image acquisition device and calibrating the image acquisition device using data from the calibration fixture. Additionally, the method may include acquiring tracking data using at least one tracking device located on the calibration device. The image acquisition device may also be modeled using the data from the calibration fixture.

In an embodiment, the method also includes characterizing the image acquisition device to improve registration between points in an image reference frame and points in a navigation reference frame. Image data obtained using the image acquisition device may be processed to reduce image artifacts. In an embodiment, the method includes analyzing image data of the calibration fixture in a frequency domain. The data may be translated from the frequency domain to a spatial domain after analysis. The data may be analyzed using a Fourier analysis and/or other analysis method(s).

Certain embodiments of an improved calibration device for calibrating an imaging system include a radiotranslucent calibration fixture capable of creating a characterization frequency used in calibrating an image acquisition device and a positioning device for positioning the calibration fixture with respect to the image acquisition device. The radiotranslucent fixture may generate low frequency data, for example, used in calibrating an image acquisition device. In an embodiment, the radiotranslucent calibration fixture comprises a plurality of peaks and valleys to generate a distinctive characterization frequency. In an embodiment, the calibration device includes a moiré pattern for use in calibrating the image acquisition device, for example.

Certain embodiments provide a method for imaging system calibration. The method includes generating a moiré pattern in acquired image data, and extracting at least one characteristic of a moiré pattern for use in calibrating the imaging system. The method may also include removing the moiré pattern from the image data to produce an output image. In an embodiment, the method may further include positioning a grating with respect to an image acquisition device to generate the moiré pattern. Additionally, the method may include calibrating the imaging system during image acquisition.

Certain embodiments provide an imaging calibration system. The system includes a grating, such as a periodic or repetitive grating, configured to produce a moiré pattern in an image, wherein said moiré pattern encodes information regarding positioning of an image acquisition device into the image, and a processor configured to calibrate positioning of the image acquisition device using the moiré pattern. In an embodiment, a plurality of gratings may be positioned to produce a moiré pattern. In an embodiment, the grating includes an x-ray grid integrated in the imaging system and configured to produce the moiré pattern, for example. An analysis, such as a Fourier analysis or other analysis, of the moiré pattern may be used to calibrate the positioning of the image acquisition device. In an embodiment, the processor is configured to remove the moiré pattern from the image after calibration of the image acquisition device.

BRIEF DESCRIPTION OF SEVERAL VIEWS OF THE DRAWINGS

FIG. 5 illustrates an example of a calibration fixture placed between a source and an image acquisition device used in accordance with an embodiment of the present invention.

Figure 1:
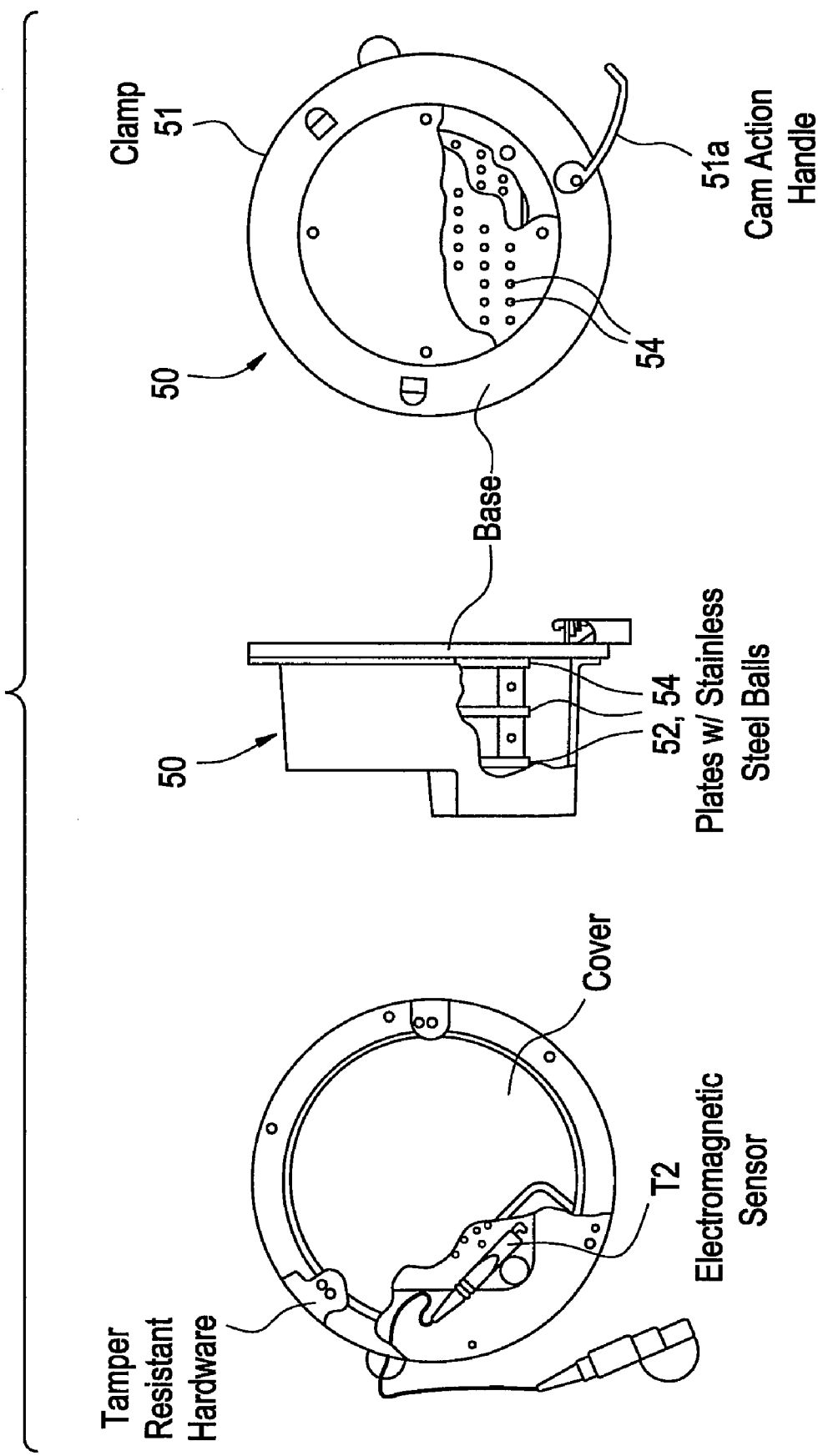
FIG. 1 illustrates an example of a calibration fixture for use in improved coordinate frame registration and tracking accuracy.
Figure 2:
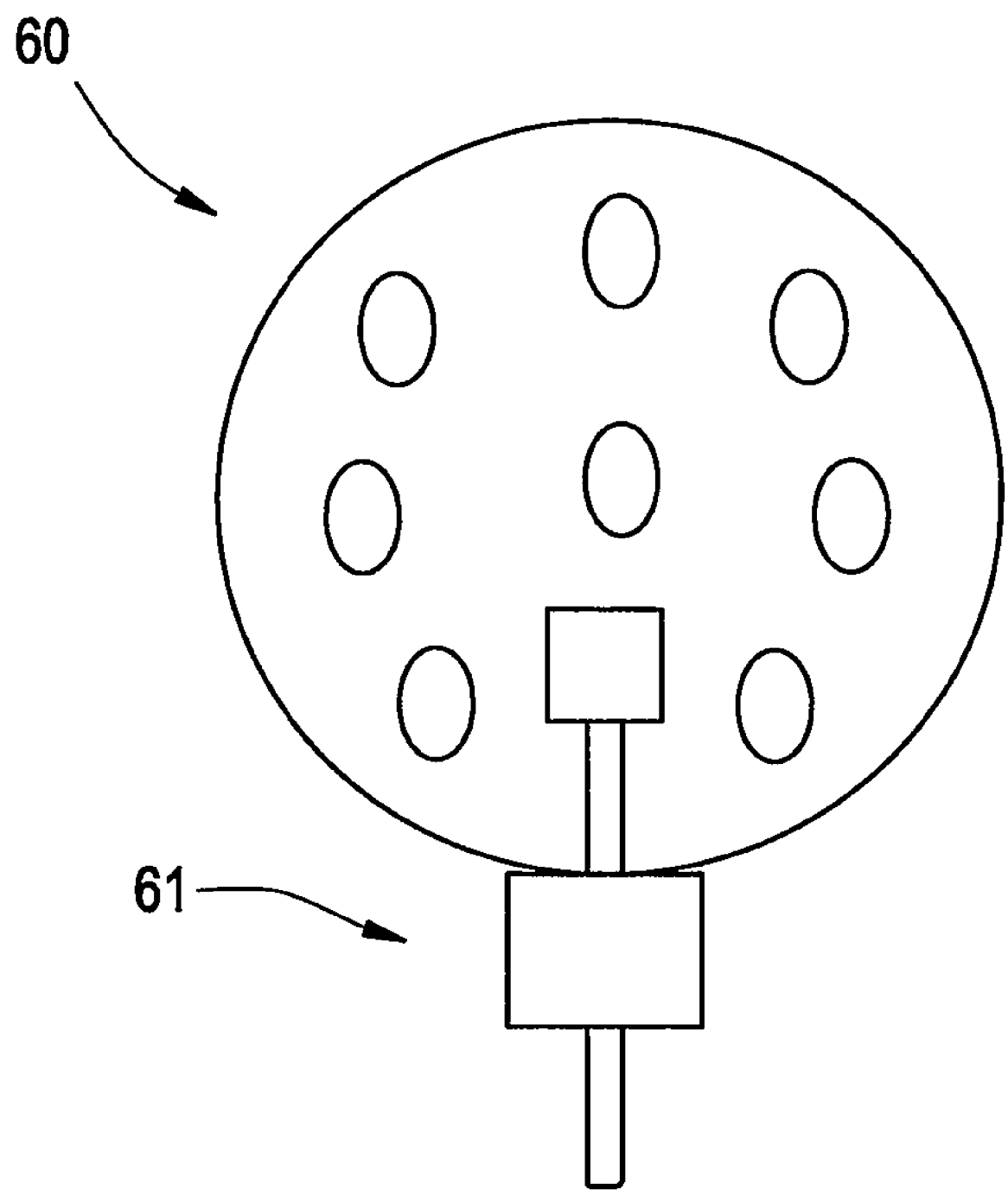
FIG. 2 illustrates another example of a calibration fixture for use in improved coordinate frame registration and tracking accuracy

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 3:
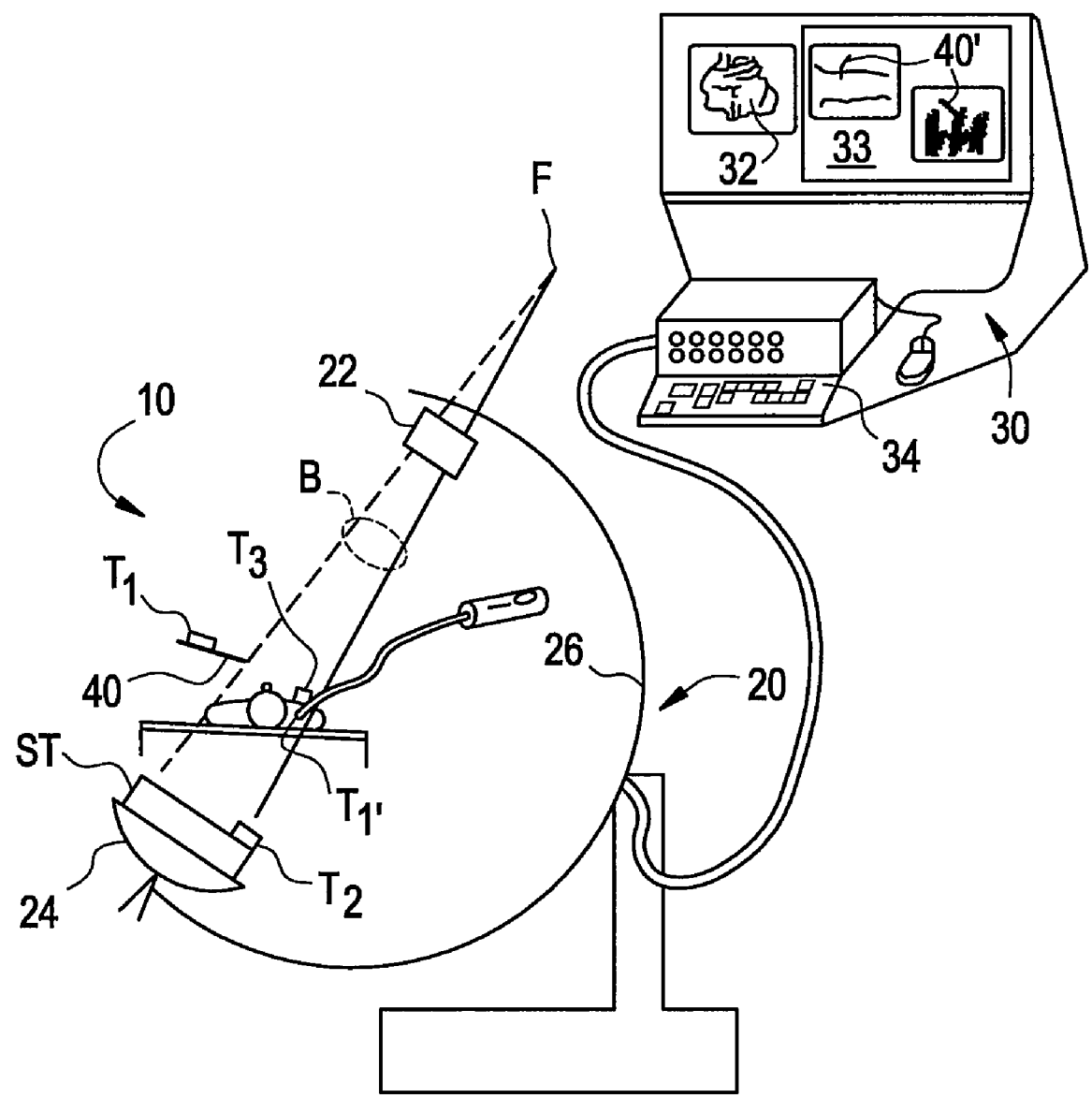
FIG. 3 illustrates an imaging system in accordance with an embodiment of the present invention for use in an operating room environment.

FIG. 3 illustrates an imaging system 10 in accordance with an embodiment of the present invention for use in an operating room environment. As shown in FIG. 3, the system 10 includes a fluoroscope 20, a work station 30 having one or more displays 32 and a keyboard/mouse or other user interface 34, and a plurality of tracking elements T1, T2, T3. The fluoroscope 20 is illustrated as a C-arm fluoroscope in which an x-ray source 22 is mounted on a structural member or C-arm 26 opposite to an x-ray receiving and detecting unit, referred to herein as an imaging assembly 24. The C-arm moves about a patient or other object to produce two dimensional projection images of the patient from different angles. The patient or object remains positioned between the source and the camera, and may, for example, be situated on a table or other support, although the patient/object may move. The tracking elements, described further below, are mounted such that one element T1 is affixed to, incorporated in or otherwise secured against movement with respect to a surgical tool or probe 40. A second tracking unit T2 is fixed on or in relation to the fluoroscope 20, and a third tracking unit T3 fixed on or in relation to the patient. The surgical tool may be a rigid probe as shown in FIG. 3, allowing the tracker T1 to be fixed at any known or convenient position, such as on its handle, or the tool may be a flexible tool, such as a catheter, flexible endoscope or an articulated tool, for example. In the latter cases, the tracker T1 is preferably a small, localized element positioned in or at the operative tip of the tool as shown by catheter tracker T1' in FIG. 3, to track coordinates of the tip within the body of the patient.

In an embodiment, a fluoroscope operates with an x-ray source 22 positioned opposite the camera or image sensing assembly 24. While in some systems, the X-ray source is fixed overhead, and the camera is located below a patient support, the discussion below will be illustrated with regard to the more complex case of a typical C-arm fluoroscope, in which the source and camera are connected by a structural member, the C-arm, that allows movement of the source and camera assembly about the patient so that the C-arm may be positioned to produce x-ray views from different angles or perspectives. In such C-arm devices, the imaging beam generally diverges at an angle, the relative locations and orientations of the source and camera vary with position due to structural flexing and mechanical looseness, and the position of both the source and the camera with respect to the patient and/or a tool which it is desired to track may also vary in different shots.

The imaging beam illustrated by B in FIG. 3 diverges from the source 22 in a generally truncated conical beam shape, and the C-arm 26 is movable along a generally arcuate path to position the source and camera for imaging from different directions. This generally involves positioning the camera assembly 24 as close as possible behind the relevant tissue or operating area of the patient, while the C-arm assembly is moved roughly about a targeted imaging center to the desired viewing angle. The C-arm or other beam structure 26 may be a somewhat flexible structure, subject to bending, deflection or sagging as the source and camera move to different positions around the patient, and the C-arm may also have other forms of dimensional variation or looseness, such as drive gear backlash, compressible elastomeric suspension components or the like, which may contribute to variations and non-repeatability of the relative disposition and alignment of the source and camera with respect to each other, and with respect to the patient, as the assembly is moved to different positions. The C-arm may also move eccentrically or translationally to allow better clearance of the patient support table. The bending deflections of the C-arm assembly may vary the actual position of the source 22 by almost a centimeter or more with respect to the image detector, and may displace the source 22 from a nominal position which may be indicated, for example, by an encoder present in the fluoroscope stand or C-arm positioning assembly.

Figure 4:
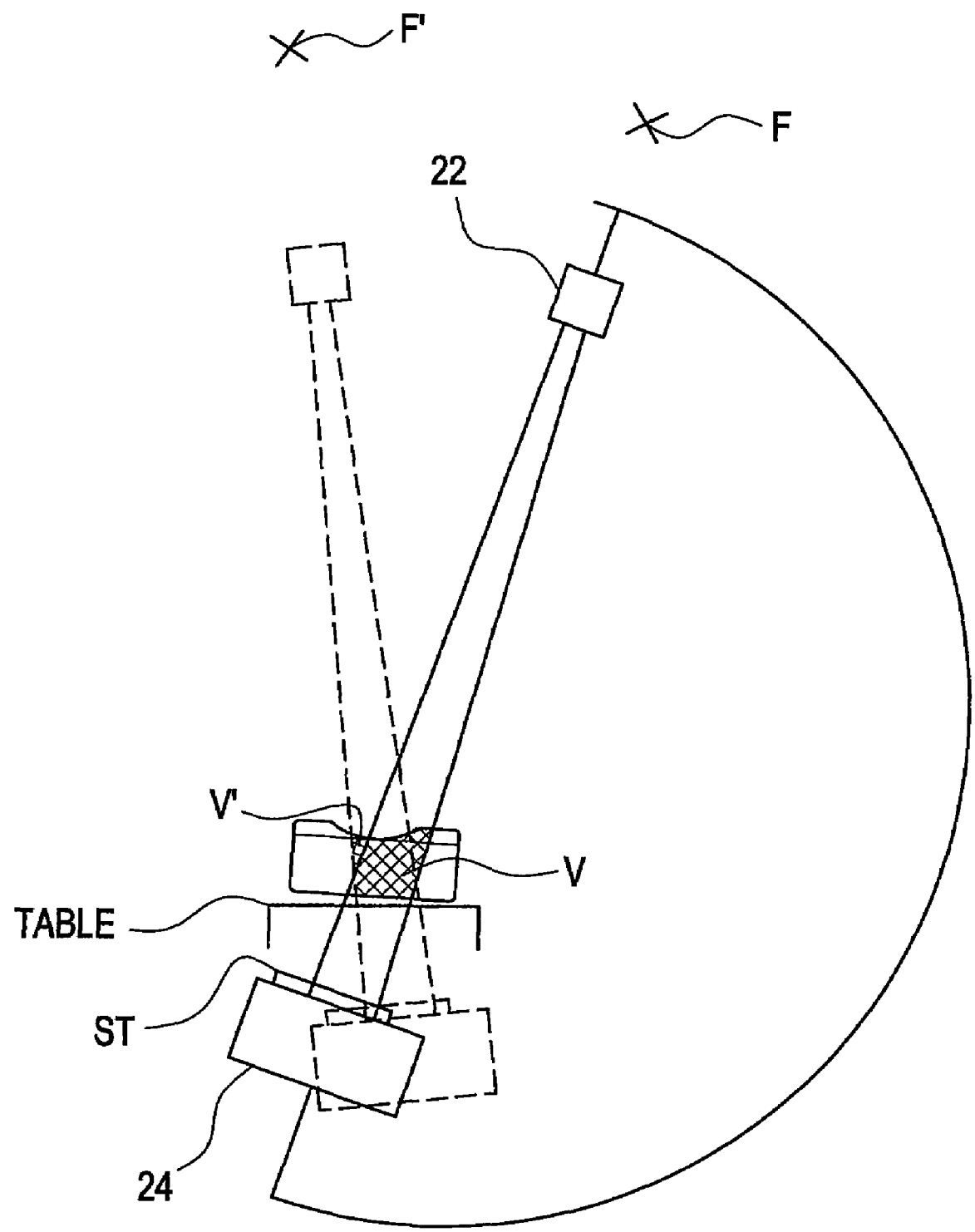
FIG. 4 illustrates a fluoroscope in two different imaging positions, with a first position shown in solid line, and a second position in dashed line phantom.

FIG. 4 illustrates the fluoroscope 20 in two different imaging positions, with a first position shown in solid line, and a second position in dashed line phantom. In the first position, a tissue volume V is imaged with a divergent beam from the above right, and a virtual beam origin or focal point at F, while the image from the second position catches a largely overlapping but partly distinct tissue volume with a divergent beam from the upper left, and a different focal point F'. The distances from points F, F' to the camera may be different, and the camera itself may shift and tilt with respect to the beam and its center axis, respectively. In practice, the x-ray beam is generally aimed by its center ray, whose intersection with the imaging plane, referred to as the piercing point, may be visually estimated by aiming the assembly with a laser pointing beam affixed to the source. The x-ray beam may be considered to have a virtual origin or focal point F at the apex of the cone beam. Generally, the camera assembly 24 is positioned close to the patient, but may be subject to constraints posed by the operating table, the nature of the surgical approach, and tools, staging, clamps and the like, so that imaging of a tissue volume somewhat off the beam center line, and at different distances along the beam, may occur. As noted above, flexing of the C-arm also changes the distance to the focal point F and this also may slightly vary the angular disposition of the beam to the camera, so this shifting geometry may affect the fluoroscope images.

Furthermore, the camera 24 may utilize an image sensing unit that itself introduces further distortions into the received distribution of image radiation. For example, the unit may involve a detector that employs a phosphor surface of generally curved contour to convert the x-ray image intensity distribution to a free electron distribution. Such a curved phosphor screen is generally placed over an electron multiplier or image intensifier assembly that provides an enhanced output video signal, but may further introduce a form of electron optical distortion that depends upon the intensifier geometry and varies with the orientation of the camera assembly in the earth's magnetic field. Other configurations of image detectors are also known or proposed, such as digital x-ray detectors or flat semiconductor arrays, which may have different imaging-end fidelity characteristics. Deflection or physical movement of the camera itself as well as electron/optical distortion from the camera geometry, image detector and variations due to gravitational, magnetic or electromagnetic fields may enter image reception and affect projective geometry and other distortion of a final image produced by the assembly.

Current imaging calibration systems use an array of discrete, dark markers for calibration, allowing a certain degree of distortion to remain in an image due to the calibration markers. In an embodiment, rather than using a discrete, dark marker, a marker or calibration fixture is used that varies image intensity very slightly over a large area. Rather than using a grid including a plurality of discrete markers, a calibration marker or fixture providing a continuously varying signal may be used. For example, a Fourier spectrum or other analysis may be obtained using data from the marker's signal. Data is converted to a frequency domain, and a frequency representing the marker is identified, interpreted, and, optionally, removed. After the marker frequency has been identified, the data is converted back to an image or spatial domain. In converting from the frequency to the spatial domain, variations, such as attenuation variations, density variations, and/or thickness variations, in the data signal may be identified. Alternatively or in addition, other image analysis techniques besides Fourier analysis may be employed to detected spatial correlations of low-contrast features and to extract calibration parameters.

Thus, rather than using visually occluding BBs or similar calibration markers, radiotranslucent markers providing a detectable, varying signal may be used for camera calibration. Signals from one or more radiotranslucent markers may be used to determine a focal length and piercing point for an imaging camera. For example, determination of a ray normal to the imaging plane that identifies where the source should be may be facilitated using a single layer of two or three radiotranslucent markers. Therefore, the camera may be modeled based on an object known with respect to a tracking reference.

Using BBs or other radiopaque markers, imaging systems interpolate image representing an area blocked by the marker based on image data obtained around the marker. Rather than using a radiopaque marker, a radiotranslucent material, such as plastic or Plexiglas, may be used. Rather than filtering out peaks in signal data indicating a location of a BB or other radiopaque marker, a distortion may be generated using a radiotranslucent marker and filtered out after the distortion frequency is identified.

Figure 6:
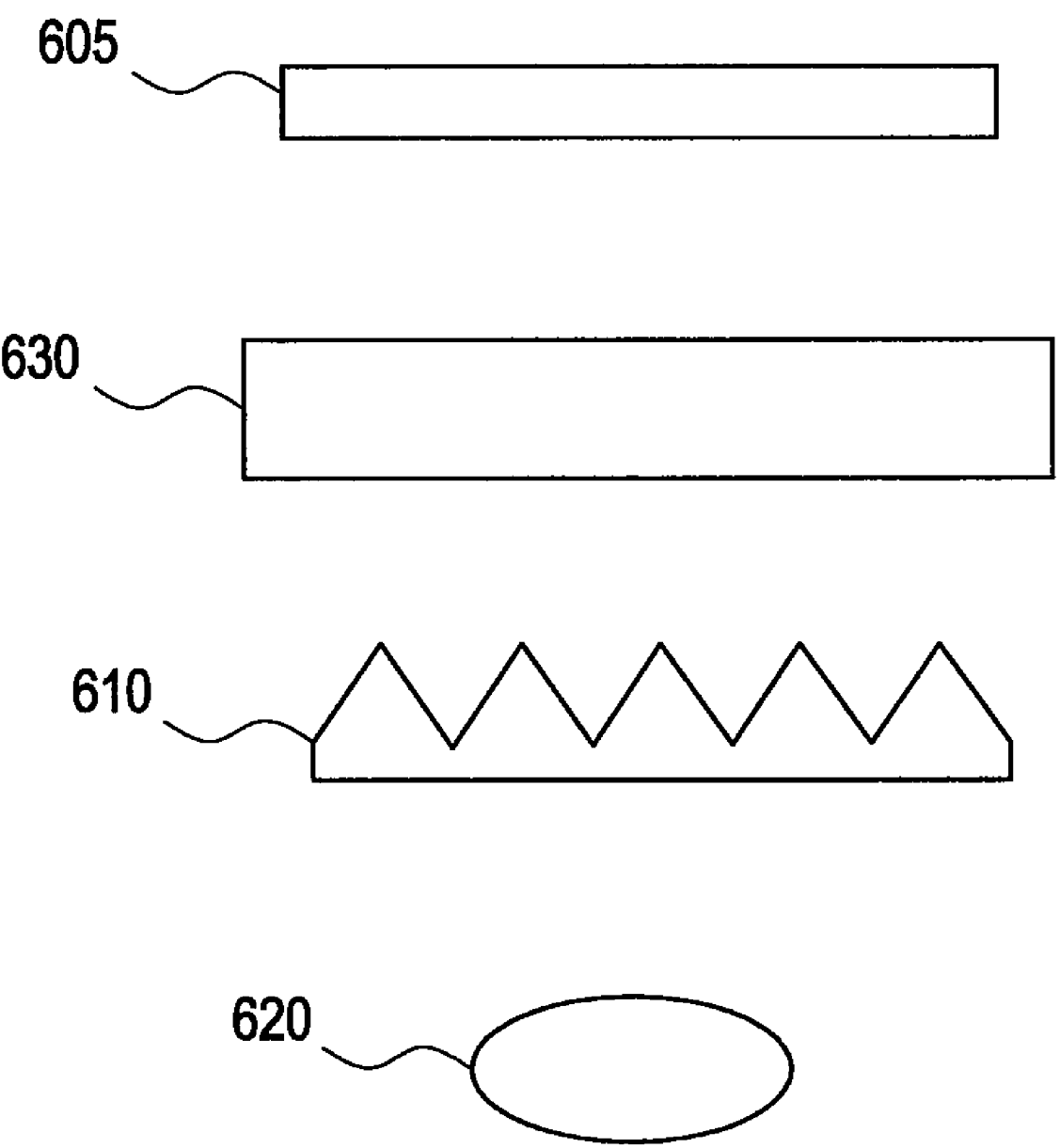
FIG. 6 shows a reflector placed behind an image acquisition device to obtain data from x-rays reflected back to the image acquisition device from an object in accordance with an embodiment of the present invention.

For example, a geometry may be constructed in relation to the camera and the object being imaged. The geometry may be used to create a distortion pattern with an easily recognizable image. The geometry may be created using a wavy panel, for example, positioned between the source and the detector. FIG. 5 illustrates an example of a wavy panel 510 placed between a source 520 and a flat panel detector 530 used in accordance with an embodiment of the present invention. In an embodiment, the wavy panel 510 includes a plurality of peaks and valleys configured to produce a low frequency calibration response. The wavy panel 510 or other low frequency radiotranslucent calibration fixture may be used to obtain distortion and characterization information for the detector 530. A positioning device, such as a radiotranslucent clamp or mounting bracket, may be used to position the panel 510 with respect to the detector. Alternatively, as shown in FIG. 6, a reflector 605 may be placed behind a detector 630, such as a flat panel detector, to obtain data from x-rays reflected back to the detector 630 from an object 640 (not shown). Alternatively, in an embodiment, a component of the imaging system, such as the detector 530 and/or x-ray grid, may be used for imaging system calibration.

A geometric panel, such as the wavy panel shown in FIG. 5, is designed to generate low frequency information. For example, the panel provides a low frequency wave that may be easily identified while providing a profile that does not excessively interfere with an obtained image. The panel generates less interference than a radiopaque marker, such as a BB, because the radiotranslucent panel allows more x-ray transmission to pass through the panel than a radiopaque marker. A radiotranslucent panel may provide a smooth, identifiable wave rather than large spikes in image data.

While radiopaque BBs are localized in obtained images, a geometric panel allows a global sweep to be made across an image to obtain calibration data in the frequency domain rather than the spatial domain. Calibration analysis may then be performed in the frequency domain using a Fourier transform and/or other method for detecting spatial correlations in an intensity field, for example, rather than in the spatial domain.

In an embodiment, since analysis is being performed in the frequency domain across the entire image and interference with image data is minimal, the source and detector of the imaging system may be positioned as close as possible, while still avoiding collisions between system components and minimizing patient discomfort. The radiotranslucent marker may be a removable component or may be integrated into a C-arm in the imaging system, for example. In an embodiment, the radiotranslucent marker provides a low-frequency response. The radiotranslucent marker may include one or more components and may be of varying thickness. For example, the radiotranslucent marker or fixture may include a plurality of coils or spirals. Alternatively, the radiotranslucent fixture may be a wavy panel including a plurality of peaks and valleys. The wavy panel may produce a pattern of variations, such as attenuation, density and/or thickness variations. The radiotranslucent fixture may include multiple levels of varying thickness and/or varying configuration to obtain more information with which to characterize the imaging camera or detector. However, a single layer marker may also be effective in providing information to characterize the camera. The radiotranslucent fixture is used to extract camera parameters, such as the focal length and piercing point, to characterize the camera.

In an embodiment, camera characterization is determined separately from navigation, such as electromagnetic (EM) tracking. For example, the camera is characterized using a calibration fixture, such as a radiotranslucent calibration fixture. In another embodiment, the radiotranslucent calibration marker may also function as a sensor. That is, a sensor and radiotranslucent calibration marker may be combined together or the tracking sensor may function as the calibration marker. Thus, camera characterization and tracking may proceed concurrently. A tracking system may track the camera and/or track the object being imaged to characterize (i.e., extract) camera parameters. The position of the object relative to the sensor may be determined by the tracking system in order to track the sensor during an image-guided operation.

In an embodiment, an 8- to 12-bit value is used to convey image data to the imaging system. A certain number of bits are used to represent an object being imaged. A remainder of bits may be used for other purposes, such as transmitting low frequency data from the calibration marker/sensor. For example, 8 of 12 bits may be used for anatomy image data, and the remaining 4 bits may be used to transmit low frequency content for tracking.

Thus, images obtained in a system using radiotranslucent calibration fixtures include very slight attenuation that is not very perceivable to the viewer. The attenuation is viewable through calibration algorithms for use in characterizing the imaging camera and registering reference coordinate frames. The minimal attenuation may be removed or reduced, if desired, through processing at a display workstation and/or an image processing workstation.

Figure 7:
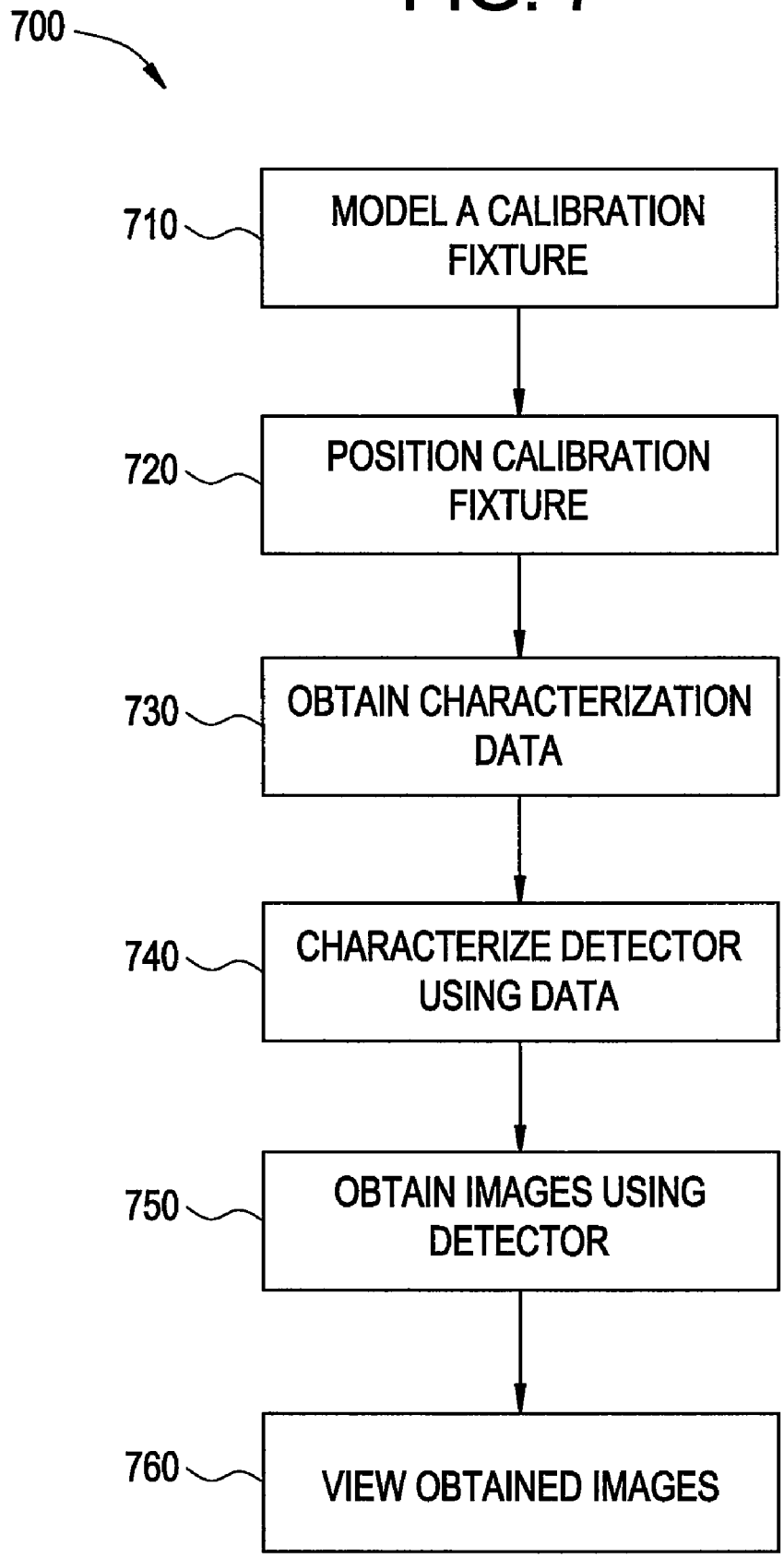
FIG. 7 illustrates a flow diagram for a method for improved characterization of an imaging camera used in accordance with an embodiment of the present invention.

FIG. 7 illustrates a flow diagram for a method 700 for improved characterization of an imaging camera used in accordance with an embodiment of the present invention. First, at step 710, a radiotranslucent calibration fixture is modeled so that the fixture may serve as a reliable reference to measure and correct registration or calibration error. The radiotranslucent calibration fixture may be measured and modeled within tight tolerances during and/or after manufacturing, for example. The radiotranslucent calibration fixture may be used as a predefined object for calibration and characterization of the imaging system.

Next, at step 720, the radiotranslucent calibration fixture is positioned between an energy source and an image acquisition device, such as an image intensifier or other detector, in relation to an object being imaged. Then, at step 730, characterization data is obtained from the radiotranslucent calibration fixture. For example, a tracking device may be attached to or integrated with the calibration fixture to obtain characterization data. Alternatively, characterization data may be obtained during a calibration scan of the object and the calibration fixture. The low frequency contribution from the radiotranslucent calibration fixture is identified and data extracted in the frequency domain using a Fourier transform or similar method for detecting spatial correlations in an intensity field, for example.

At step 740, the detector or camera, such as an image intensifier, of the imaging system is characterized using data obtained from the radiotranslucent calibration fixture. That is, the camera, as well as relationships between the calibration fixture, camera, and source, may be modeled. Coordinates in a camera or image coordinate system and a navigation or tracking coordinate system may be correlated using characterization data. Thus, the imaging system may be calibrated for imaging and image-guided operations.

Then, at step 750, one or more images of the object may be obtained using the image acquisition device. At step 760, obtained images may be viewed by an operator, such as a surgeon. If desired, the images may be "cleaned up" to remove distortion caused by the radiotranslucent calibration fixture or other artifact. For example, the low frequency response from the radiotranslucent calibration fixture may be identified and filtered from the image data. The calibration and imaging step of the method 700 may be repeated before each imaging session and/or between images, depending upon circumstances and/or operator instructions.

Alternatively or in addition, geometry-sensitive image patterns, such as moiré patterns, may be implemented for calibration of an imaging system. In certain embodiments, moiré patterns may be generated using existing components of an x-ray system, such as an x-ray scatter grid or other grating. Certain embodiments provide intrinsic calibration of an imaging system more precisely, without user intervention, and without using a separate calibration device. Certain embodiments use moiré patterns produced by slightly modified existing components of an x-ray image acquisition chain (e.g., an x-ray scatter grid, a flat panel detector, a CCD pixel grid, and/or image processing) to measure intrinsic geometry parameters of an imaging system.

Moiré patterns arise when two or more basis patterns are juxtaposed and combined non-linearly, e.g. multiplicatively. If the basis patterns are periodic gratings, then the moiré pattern may contain harmonics of lower and higher frequencies than the frequencies in either periodic grating, for example. Small spatial shifts of the basis patterns may produce easily detectable large phase shifts or frequency shifts in the moiré pattern. Generation of large phase or frequency shifts based on small spatial shifts allow measurement of microscopic geometric offsets and distortions.

A combination of two periodic patterns generate waves or moiré patterns that may be used to identify characteristics of an imaging system, for example. Two high-frequency gratings (e.g., main frequency of 10 lines/mm) positioned a small distance (e.g., 1 cm) apart may generate a low frequency wave moiré pattern (e.g., a 10 mm wavelength) in a diverging x-ray beam (e.g., with an x-ray focal spot 100 cm away). Moiré patterns may exaggerate or magnify offset(s) in an imaging system. Moiré patterns may produce wavy patterns similar to or in substitution for the calibration fixture described above, for example. One or more gratings may be constructed or transparent and/or non-transparent material. For example, grating(s) of fine lead thread may be constructed and positioned so that attenuation or other similar effect is produced by a periodic pattern of absorbing and non-absorbing parts.

An imaging chain of a fluoroscopic system may include some periodic gratings that are combined multiplicatively, for example. For example, a transmittance function of an x-ray scatter grid and a sensitivity function of a pixel array of an x-ray detector are effectively multiplied into a final image. Other gratings may be inserted artificially in a way that would have only a minimal impact on image quality. If the two gratings are placed parallel to one another a small distance apart, then the motion of the x-ray focal spot relatively to this assembly will produce predictable changes in the moiré pattern.

Figure 8:
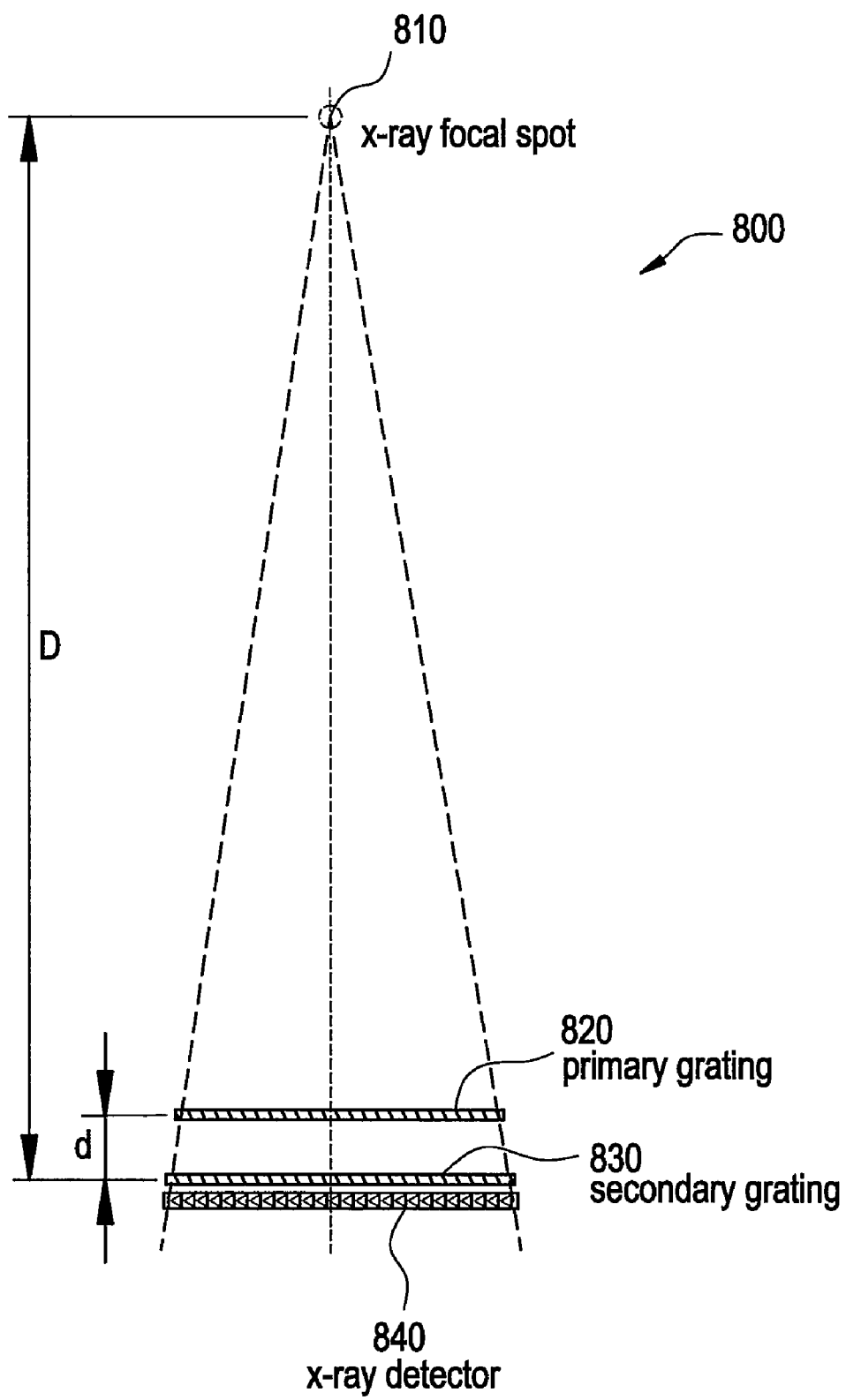
FIG. 8 illustrates an example of a moiré-based geometry calibration system used according to an embodiment of the present invention.

FIG. 8 illustrates an example of a moiré-based geometry calibration system 800 used according to an embodiment of the present invention. The calibration system 800 includes an x-ray focal spot 810, a primary grating 820, and secondary grating 830, and an x-ray detector 840. The calibration system 800 may help determine or refine a location of an x-ray focal spot using a primary grating and a secondary grating positioned with respect to an x-ray detector. As shown in FIG. 8, d represents a distance between the primary grating and the secondary grating. D represents a distance between the x-ray source focal spot and the secondary grating/x-ray detector.

In an embodiment, two or more superposed gratings placed at a small distance apart may be used to produce a moiré pattern for intrinsic geometry calibration. That is, attenuation patterns of the gratings interfere to produce a third attenuation pattern that may be highly sensitive to a position of a focal spot. After a moiré pattern is detected and analyzed, the pattern may be removed digitally from an image with minimal effect on image quality.

Several devices may be employed as superposed gratings in an x-ray beam. One grating may be an anti-scatter grid (e.g., an aluminum or carbon-fiber substrate with embedded lead strips), for example. Both linear and cross anti-scatter grids may be used. Normally, anti-scatter grids are designed to minimize any moiré patterns produced by interference with the detector pixel grid. However, a grid may be designed to maximize the moiré patterns from interference with an x-ray detector for use in geometry calibration. Thus, an x-ray detector itself may be used as another grating. A detector's pixels and inter-pixel spaces may naturally form a cross grating. A "digital grating" may also be introduced. That is, an image may be digitally multiplied with a periodic pattern to induce a moiré pattern. In an embodiment, two superposed anti-scatter grids may be used to produce a moiré pattern from interference between them. In other embodiments, an additional grating may inserted into the optical portion of an x-ray detector after x-ray have been converted into visible light, for example, but before digitization. This approach may produce higher detector quantum efficiency since the grating is introduced in a non-quantum-limited portion of the image chain.

In an embodiment, a cross grating may be used to detect the location of an x-ray focal spot in three dimensions. Alternatively, line gratings at various angles may be used in limited portions of an x-ray image to achieve the same goal.

In an embodiment, intrinsic geometry parameters for the x-ray imaging system may be recovered from a moiré pattern using the following method. For example, let $$p_1(x) = \frac{1}{2} + \frac{1}{2}\cos(2\pi v_1 x) \text{ and } p_2(x) = \frac{1}{2} + \frac{1}{2}\cos(2\pi v_2 x)$$

be the respective transmittance functions of a primary line grating and a parallel secondary line grating. Here, x is a spatial dimension. For purposes of simplicity, each grating is represented as a single harmonic with the respective frequencies $v_1$ and $v_2$ cycles per mm. Although a plurality of configurations may be chosen, the following example illustrates a case when $v_1=v_2=v$. The grating frequencies $v_1$ and $v_2$ may be selected to be above a limiting resolution of the image acquisition process. However, moiré patterns resulting from superposition may be detectable. Let $d_1$ and $d_2$ be respective distances from the x-ray focal spot to the primary and secondary gratings. Let $x_0$ be an x-coordinate of the x-ray focal spot. Then, $p_1(x)$ projects onto the coordinate plane of the secondary grating as $$p'_1(x) = p_1\left(\frac{d_1}{d_2}(x - x_0)\right).$$

Let u represent spatial frequency. Let $\delta(u)$ be a Dirac delta function and $\delta(u\pm v)=\delta(u+v)+\delta(u-v)$. Then, transmittance functions of the two gratings may be transformed into the Fourier domain as:

$$p'_1(x) =$$

$$\frac{1}{2} + \frac{1}{2}\cos\left[2\pi \frac{d_1}{d_2}(x-x_0)\right] \overset{\text{Fourier}}{\longleftrightarrow} P'_1(u) = \frac{1}{2}\delta(u) + \frac{1}{4}\delta\left(u \pm \frac{d_1}{d_2}v\right)e^{-i2\pi u x_0}$$

$$p_2(x) = \frac{1}{2} + \frac{1}{2}\cos[2\pi v x] \overset{\text{Fourier}}{\longleftrightarrow} P_2(u) = \frac{1}{2}\delta(u) + \frac{1}{4}\delta(u \pm v).$$

A Fourier representation of a combined transmittance function $$m(x) \overset{\text{Fourier}}{\longleftrightarrow} M(u)$$

of the two gratings is then:

$$m(x) = p'_1(x)p_2(x) \overset{\text{Fourier}}{\longleftrightarrow} M(u) = P'_1(u) * P_2(u)$$

$$M(u) = \frac{1}{16} \times \left[4\delta(u) + \underbrace{\delta\left(u \pm \left(1 - \frac{d_1}{d_2}\right)v\right)e^{-i2\pi u x_0}}_{\text{Moiré pattern}} + \right.$$

$$\left. \underbrace{\delta\left(u \pm \left(1 + \frac{d_1}{d_2}\right)v\right)e^{-i2\pi u x_0} + 2\delta(u \pm v) + 2\delta\left(u \pm \frac{d_1}{d_2}v\right)}_{\text{high frequencies undetected by the image acquisition process}} \right] =$$

$$\frac{1}{4}\delta(u) + \underbrace{\frac{1}{16}\delta\left(u \pm \left(1 - \frac{d_1}{d_2}\right)v\right)e^{-i2\pi u x_0}}_{\text{Moiré' pattern}}$$

Thus the two gratings introduce a low-frequency moiré pattern that may be detectable in the Fourier domain as a distinct spike even in the presence of other image information. Once detected, the moiré pattern provides two pieces of information: a ratio $d_1/d_2$ and an offset $x_0$. If, in place of the one-dimensional line gratings in the example above, two-dimensional cross gratings were used, the moiré pattern would also yield the orthogonal offset $y_0$. With a known physical distance separating the gratings, these three pieces of information yield a complete position of the x-ray focal spot in relation to the gratings.

Once the moiré pattern is detected and interpreted, the moiré pattern may be subtracted or otherwise removed from the obtained image by digital image processing. That is, using information describing the detected moiré pattern, acquired image data may be corrected to eliminate the effects of the moiré pattern in the image. Thus, a user may be unaware of the moiré pattern that has been used to assist in calibration of the imaging system. Alternatively, an effect of a moiré pattern may be within acceptable tolerances and may be left in a resultant image, for example.

Certain embodiments provide high sensitivity in moiré pattern detection and imaging system calibration. The moiré pattern in the example above shifts by $$\frac{d_1}{d_2 - d_1}x_0$$

when the focal spot moves by $x_0$. If $$\frac{d_1}{d_2} = 0.98,$$

for example, movement of the focal spot is magnified by a factor of 49. Detecting an offset of such a moiré pattern with an accuracy of ±2 mm, for example, results in an effective calibration accuracy of ±0.04 mm.

Figure 9:
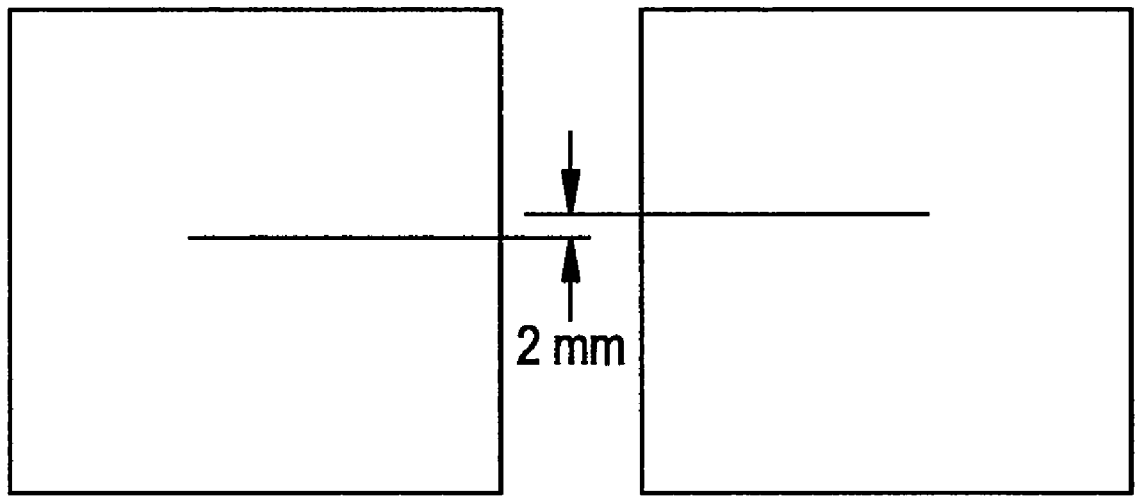
FIG. 9 shows an example of pixel moiré patterns produced by an x-ray scatter cross grid placed above a detector pixel array in accordance with an embodiment of the present invention.

FIG. 9 shows an example of a moiré pattern produced by two a 5 cycles/mm cross gratings placed 20 mm apart. A distance to the x-ray focal spot is 100 cm. A period of the resulting moiré pattern is 10 mm, and an offset magnification factor is 50. In the pattern on the right, the focal spot was moved by 0.04 mm vertically. This focal spot shift caused an offset of the moiré pattern by 2 mm. System designers may choose various grating frequencies and distances between gratings to achieve a desired calibration sensitivity and range.

Figure 10:
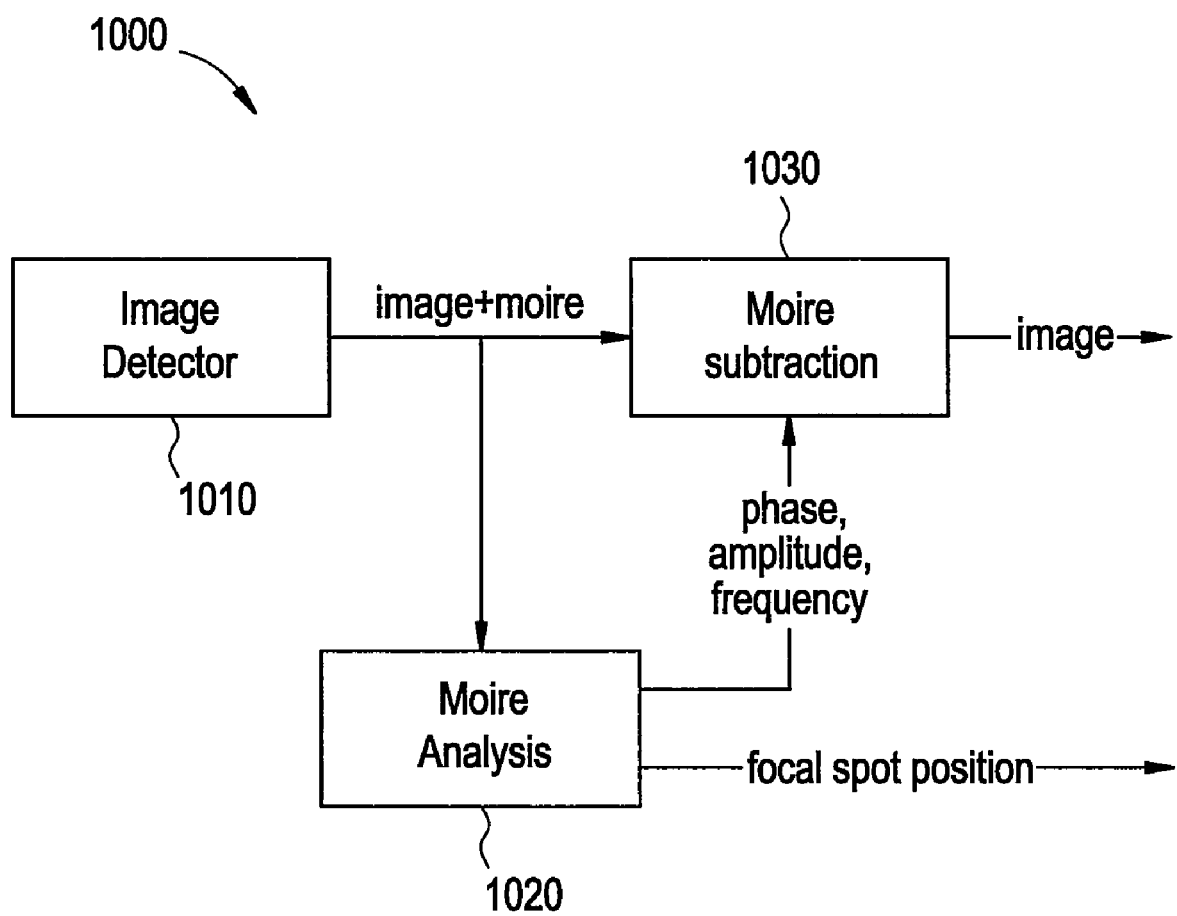
FIG. 10 illustrates a diagram of a dataflow for moiré-based geometry calibration of an imaging system used in accordance with an embodiment of the present invention.

FIG. 10 illustrates a diagram of a dataflow 1000 for moiré-based geometry calibration of an imaging system. The dataflow 1000 includes an image detector 1010, a moiré analysis unit 1020, and a moiré subtraction unit 1030. The image detector 1010 detects an image including a moiré pattern. The moiré pattern may be generated by one or more gratings, radiotranslucent panels, and/or other structure, for example. The image detector 1010 collects data representative of an object, such as a patient, being imaged plus moiré pattern data from the grating, detector, panel, or other device used to generate the moiré pattern. The image plus moiré pattern is transmitted to the moiré analysis unit 1020. The moiré analysis unit 1020 identifies an x-ray focal spot position from phase, amplitude, and frequency of the moiré pattern. The phase, amplitude and frequency data may be transmitted to the moiré subtraction unit 1030. Thus, the moiré pattern is analyzed and removed from the image. Moiré pattern data may be subtracted and/or otherwise removed from image data to produce a resultant image for use by a healthcare practitioner or other user. In an embodiment, additional image processing may be performed on the image data to remove other artifact and/or offset data, for example. The phase and the frequency of the moiré pattern are used to compute the focal spot position in the detector coordinate system, for example.

Figure 11:
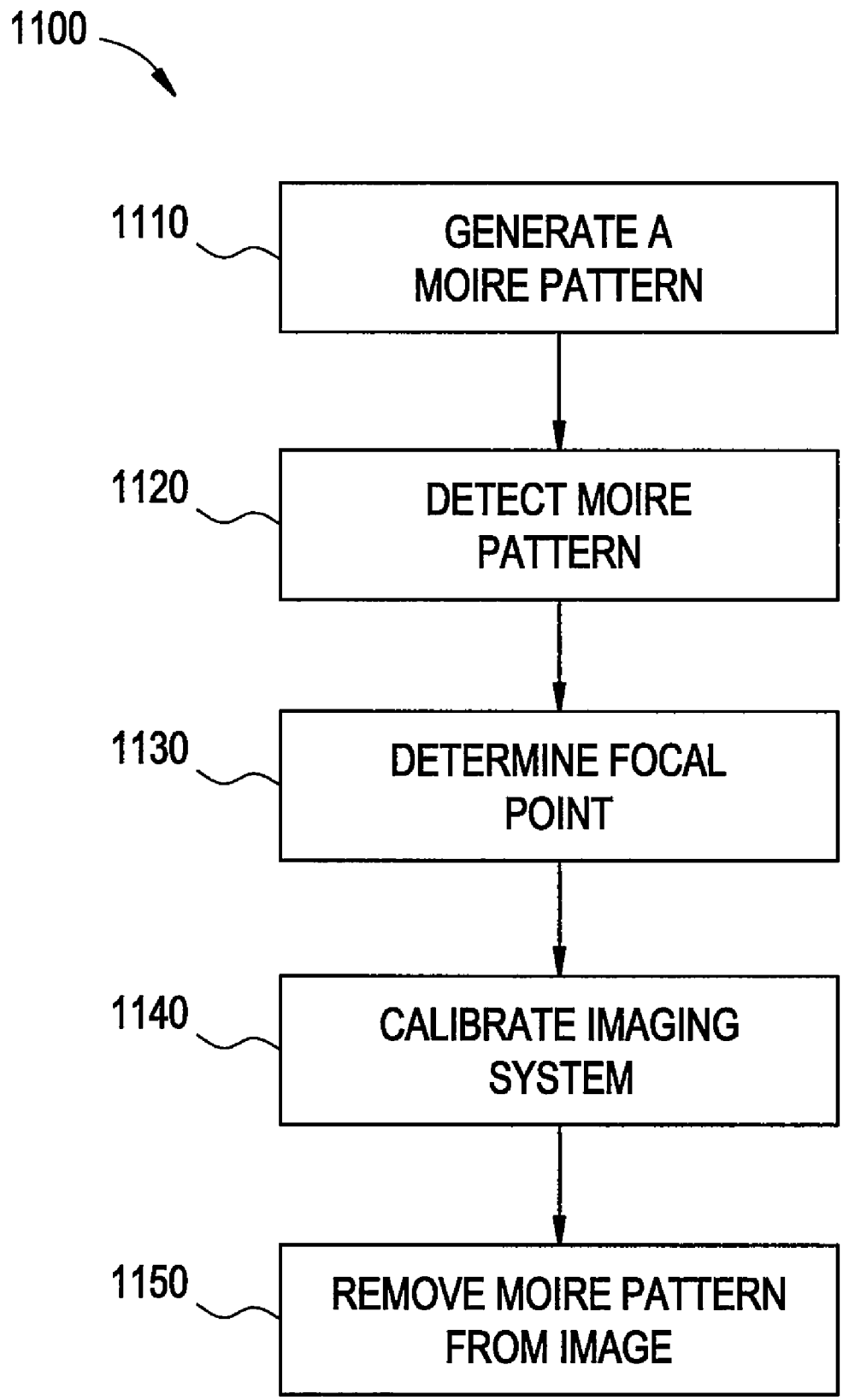
FIG. 11 illustrates a flow diagram for a method for used in accordance with an embodiment of the present invention.

FIG. 11 illustrates a flow diagram for a method 1100 for used in accordance with an embodiment of the present invention. First, at step 1110, a moiré pattern is generated using one or more gratings positioned with respect to an imaging system. For example, two thin metal gratings may be positioned slightly offset from each other in front of an x-ray detector to generate a moiré pattern in an image obtained using the detector. In an embodiment one grating may be offset from the detector to create a moiré pattern between the grating and the detector. Alternatively, more than two gratings may be used to create a moiré pattern.

Then, at step 1120, the moiré pattern is detected. The moiré pattern may be detected via image processing in an obtained image, for example. The moiré pattern may be obtained in a calibration image and/or a patient exposure image, for example. The moiré pattern may also be detected by a sensor aside from an image acquisition system, for example. For example, frequency patterns or interference introduced in the image based on the grating(s) may be detected in the image.

Next, at step 1130, an x-ray focal point is determined with respect to the grating(s) based on one or more characteristics of the moiré pattern. For example, characteristics of the moiré pattern found in the image may be used to generate a focal point distance and location to aid in calibration of imaging system to accommodate for variations in positioning, etc. At step 1140, the x-ray imaging system is calibrated based on the focal point and/or other characteristic information. For example, movement in the focal point from an expected or default position for the focal point may be used to calibrate or accommodate for differences in positioning between the x-ray source and x-ray detector.

Then, at step 1150, the moiré pattern is removed from the resultant image. That is, after characteristics of the moiré pattern have been used to calibrate the imaging system, the moiré pattern may be removed from the image to provide a clearer image to a user. In an embodiment, moiré pattern interference may be relatively undetectable to a user and may remain in the image. However, in another embodiment, moiré pattern interference may be removed from the image to minimize distortion and/or artifacts in the image displayed to a user. One or more image processing techniques may be used to filter out the moiré pattern interference from the image data. For example, the moiré pattern produces a known interference that may be subtracted from image data obtained by the detector to produce a resultant image for store, display, transmission, etc. In an embodiment, additional image processing may also be performed on the image data.

Thus, certain embodiments provide intrinsic calibration procedures without a particular calibration device or phantom if existing system components are configured to induce moiré patterns in acquired images. Certain embodiments reduce or eliminate a separate calibration procedure by performing calibration during normal imaging operation. Calibration error due to scan-to-scan differences may be reduced or eliminated by performing on-line calibration. Certain embodiments may perform calibration in real-time using off-the-shelf DSP (digital signal processing) components. Certain embodiments use moiré pattern analysis for intrinsic geometry calibration in x-ray or other applications. Certain embodiments utilize the high sensitivity of moiré patterns to measure microscopic shifts in an imaging system.

Certain embodiments of the present invention also provide an artifact positioned with respect to and away from an imaging surface to create a model of a relative position of a source in relation to an image camera, such as an image intensifier. Certain embodiments provide additional artifacts to pick up image distortion. Certain embodiments allow calibration markers to be moved closer to an object being imaged. Certain embodiments map between a model of the calibration fixture and obtained data points from the calibration fixture to create a local mapping. With flat panel detector, for example, an exact relationship between the geometry of the calibration fixture and the image may be determined. Certain embodiments of the present invention provide a calibration fixture that minimizes its effect on a resulting image while providing information to calibrate and characterize the imaging system.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system facilitating calibration of an image acquisition device, said system comprising:
   an image acquisition device for obtaining at least one image of an object;
   a calibration fixture positioned in relation to said image acquisition device, wherein said calibration fixture includes a radiotranslucent material providing low frequency content for characterizing said image acquisition device; and
   a filter configured to filter from the obtained image distortion due to the radiotranslucent material.

2. The system of claim 1, wherein said calibration fixture includes at least one of density and thickness variations to create a low frequency signal for characterizing said image acquisition device.

3. The system of claim 1, wherein said calibration fixture is positioned between said image acquisition device and an energy source such that a distance between said calibration fixture and said energy source is minimized.

4. The system of claim 1, further comprising at least one tracking device for obtaining at least one of position and orientation data for said calibration fixture.

5. A method for calibration of an image acquisition system, said method comprising:
   acquiring image data of a radiotranslucent calibration fixture located near an image acquisition device;
   calibrating said image acquisition device using image data of said calibration; and
   filtering from the acquired image data distortion due to said radiotranslucent calibration fixture.

6. The method of claim 5, further comprising acquiring tracking data using at least one tracking device located on said calibration fixture.

7. The method of claim 5, further comprising modeling said image acquisition device using said image data from said calibration fixture.

8. The method of claim 5, further comprising analyzing said image data of said calibration fixture in a frequency domain.

9. The method of claim 8, further comprising translating said image data from said frequency domain to a spatial domain.

10. The method of claim 5, further comprising analyzing said image data from said calibration fixture using a Fourier analysis.

11. The method of claim 5, wherein said calibration fixture generates low frequency data used to calibrate said image acquisition device.

12. The method of claim 5, further comprising characterizing said image acquisition device to improve registration between points in an image reference frame and points in a tracking reference frame.

13. The method of claim 5, further comprising processing said image data obtained using said image acquisition device to reduce image artifacts.

14. A calibration device for calibrating an imaging system, said calibration device comprising:
- a radiotranslucent calibration fixture capable of creating a characterization frequency used in calibrating an image acquisition device;
- a positioning device for positioning said radiotranslucent calibration fixture with respect to said image acquisition device; and
- a filtering device for filtering from an acquired image distortion due to the radiotranslucent calibration fixture.

15. The calibration device of claim 14, wherein said radiotranslucent calibration fixture generates low frequency data used in calibrating an image acquisition device.

16. The calibration device of claim 14, wherein said radiotranslucent calibration fixture comprises at least one of density and thickness variations to generate a distinctive characterization pattern.

17. A calibration device for calibrating an imaging system, said calibration device comprising:
- a calibration fixture capable of creating a characterization frequency used in calibrating an image acquisition device, said calibration fixture generating a low frequency pattern used in calibrating said image acquisition device;
- a processor configured to model said image acquisition device using data from said low frequency pattern generated by said calibration fixture;
- a positioning device for positioning said calibration fixture with respect to said image acquisition device; and
- a filtering device for filtering from an acquired image distortion due to the calibration fixture.

18. The calibration device of claim 17, wherein said calibration fixture includes a radiotranslucent material providing low frequency content for characterizing said image acquisition device.

19. The calibration device of claim 17, wherein said calibration fixture generates low frequency data used in calibrating said image acquisition device.

20. The calibration device of claim 17, wherein said calibration fixture comprises a wavy panel.

21. The calibration device of claim 20, wherein the wavy panel includes a plurality of peaks and valleys configured to produce a low frequency calibration response.

22. The calibration device of claim 17, wherein said calibration fixture comprises at least one of density and thickness variations to generate a distinctive characterization pattern.

23. The calibration device of claim 17, wherein said calibration fixture is positioned between said image acquisition device and an energy source such that the distance between said calibration fixture and said energy source in minimized.

* * * * *